United States Patent [19]

Li

[11] Patent Number: 5,947,104
[45] Date of Patent: Sep. 7, 1999

[54] MANUALLY-OPERATED HYDRAULIC LINEAR ACTUATORS

[76] Inventor: Kwok-Kueng Li, 2575 SW. 83rd Ave., Portland, Oreg. 97225

[21] Appl. No.: 08/876,499

[22] Filed: Jun. 16, 1997

Related U.S. Application Data

[63] Continuation-in-part of application No. 08/380,829, Jan. 30, 1995, Pat. No. 5,638,805.

[51] Int. Cl.$^6$ .................................................. B28D 1/26
[52] U.S. Cl. .......................... 125/23.01; 125/40; 100/271
[58] Field of Search ................... 125/23.01, 40, 125/8; 100/270, 271

[56] References Cited

U.S. PATENT DOCUMENTS

| | | |
|---|---|---|
| 1,487,595 | 3/1924 | Peterman . |
| 2,657,681 | 11/1953 | Gatzke . |
| 2,779,324 | 1/1957 | Schlough et al. . |
| 2,874,688 | 2/1959 | Biesanz, Sr. et al. . |
| 2,933,079 | 4/1960 | Gutting . |
| 3,095,190 | 6/1963 | Freund ..................................... 100/270 |
| 3,161,190 | 12/1964 | Stephens et al. . |
| 3,392,719 | 7/1968 | Clanton et al. . |
| 3,686,922 | 8/1972 | Bley ....................................... 100/270 |
| 4,944,091 | 7/1990 | Johnson . |

OTHER PUBLICATIONS

Document A (Brochure for a Trimmer), Kwok–Kueng Li, pre–1995.
Document B (Operating Instructions for a Hydraulic Rock Trimmer), Kwok–Kueng Li, pre–1995.

*Primary Examiner*—Robert A. Rose
*Attorney, Agent, or Firm*—Smith-Hill and Bedell

[57] ABSTRACT

A linear actuator, which may be used as a rock trimmer, comprises a support member extending upwardly from a work surface, and a first cleaving member coupled to the support member so as to be disposed above the rock sample opposite the work surface, the first cleaving member having a working axis. The linear actuator also comprises a positioning mechanism and a hydraulic mechanism, each being operatively associated with the first cleaving member. The positioning mechanism provides for imparting rectilinear travel to the first cleaving member so as to selectively adjust the position of the member relative to the work surface, along the working axis. The hydraulic mechanism produces a working force that is transmitted to the first cleaving member for application to the rock sample. The force is applied to the sample, directed downwardly toward the work surface substantially along said working axis. The positioning mechanism and hydraulic mechanism are constructed so as to have a common actuator.

17 Claims, 8 Drawing Sheets

MANUALLY-OPERATED HYDRAULIC LINEAR ACTUATORS

CROSS REFERENCE TO RELATED APPLICATION

The present application is a continuation-in-part of copending U.S. patent application No. 08/380,829 filed Jan. 30, 1995, now U.S Pat. No. 5,638,805.

BACKGROUND OF THE INVENTION

This invention relates to manually-operated hydraulic linear actuators.

A linear actuator may be used for applying a force to a receiving member, such as a tool acting on a workpiece to move the workpiece relative to another member or to cut the workpiece or to compress the workpiece. For example, a linear actuator may be used in a rock trimmer to apply a force to a cutter for cleaving a rock sample into two or more pieces, each piece having a newly-produced face formed substantially along the cleaving line. Use of rock trimmers is generally preferred over saws and other mechanisms because trimmers produce faces that are substantially undamaged.

Although using rock trimmers is desirable, known forms of manually-operated rock trimmers have significant shortcomings. One form of rock trimmer employs a threaded member disposed through a frame, the frame being mounted on supports above a platform having a blade fitted thereon. The threaded member has a cutter at one end and a crank at the other end. By turning the crank in one direction, the threaded member is retracted in the frame away from the platform so that the trimmer can receive a rock sample on the blade. By turning the crank in the other direction, the threaded member is advanced downwardly toward the blade and platform so that the cutter engages the rock sample, the crank then being turned further to advance the cutter to cleave the sample into pieces.

This first form of rock trimmer has several important shortcomings, including that the mechanical advantage afforded by the crank is constrained by practical and operational limitations, particularly by the length of the crank and the pitch of the threads. For example, lengthening the crank to increase mechanical advantage can result in cumbersome and unstable operation, and also negate the compactness and impede the portability of the trimmer. Instability is particularly troublesome, and possibly hazardous to the operator and surrounding property. Instability arises due to the operator's application of force to the crank in a plane normal to the direction of cleaving and at a position above the rock sample, thereby introducing both tilting and rotational moments to the trimmer.

In turn, decreasing the pitch of the threads, while desirable to increase mechanical advantage, can result in unsuitably slow and mechanically-inefficient operation. Slow operation results because the number of turns of the crank necessary to retract and advance the member increases with decreasing pitch. Inefficient operation results because of friction between the threads and the frame. In particular, when the cutter is driven to cleave the rock sample, friction between the threads and frame increases. Friction requires the operator to do more work to cleave the sample than would be necessary in the absence of friction.

Another form of rock trimmer adds a hydraulic pump to the platform of the first trimmer. The pump holds the blade at the end of the pump piston, and is operated by a lever disposed under the rock sample, adjacent the platform. In this trimmer's operation, the crank is turned one way to retract the threaded member so that the trimmer can receive the rock sample on the blade and, then, the crank is turned the other way to advance the member so that the cutter and blade engage the sample. Once the sample is engaged, the hydraulic pump is actuated by pumping the lever, driving the blade upwardly toward the cutter to cleave the sample into pieces.

The second form of trimmer has several important shortcomings. For example, because the hydraulic pump is disposed below both the cutter and blade, debris produced from cleaving drops onto the extended pump piston. When the piston is later retracted, the debris can be drawn between the piston and its cylinder and possibly into the pump itself. In that event, the debris can degrade the pump's performance and can even cause pump failure, including by failure of the pump's seals.

The pump's disposition introduces other shortcomings, including several that are particularly troublesome when cleaving a relatively heavy, hard rock that protrudes beyond the dimensions of the trimmer. For example, operation of the pump's lever can be awkward due to its disposition below the rock and, therefore, can be difficult to reach and to pump. In addition, operation can also cause injury to the operator, including if one or more cleaved pieces of the rock fall from the elevated blade down onto the operator's pumping hand or if the operator strikes his hand on the rock during pumping, possibly repeatedly. Also, operation of this trimmer is manually inferior in that the pumping operation uses a lever that is isolated from the crank of the threaded member. That is, the operator is required to change hand positions between the lever and the crank in order to operate the trimmer. Moreover, the pumping action is applied to the trimmer at a location that not only reduces the operator's pumping leverage, but also impairs the operator's use of their pumping hand to counteract undesirable moments to which the trimmer can be subject. Furthermore, proper cleaving may be impeded due to reduced overall rigidity between the cutter and blade. Reduced rigidity arises because the cutter and blade both have free play and because cleaving force is not directed toward the platform and supporting structure; instead, cleaving force is directed from the blade disposed at the end of the extended pump piston upwardly away from the platform and through the cutter disposed at the end of the extended threaded member.

Accordingly, there is a need for an improved manually-operated rock trimmer that overcomes these and other limitations of conventional trimmers, particularly trimmers employing hydraulic mechanism.

SUMMARY OF THE INVENTION

The present invention fulfills the aforementioned need for an improved manually-operated rock trimmer, overcomes the limitations of conventional rock trimmers and provides advantages not heretofore available in such trimmers, by providing a novel and improved manually-operated hydraulic rock trimmer for receiving, at an associated work surface, a rock sample to be cleaved, the rock trimmer comprising a support member extending upwardly from the work surface, a first cleaving member coupled to the support member so as to be disposed above the rock sample opposite the work surface, and a positioning mechanism and a hydraulic mechanism, each operatively associated with the first cleaving member. The first cleaving member has a cleaving axis. The positioning mechanism imparts rectilinear travel to the first cleaving member so as to selectively adjust the position of the first cleaving member relative to the work surface and, therefore, the received sample, along the cleaving axis. The hydraulic mechanism produces a cleaving force, and transmits that force to the first cleaving member so that the first cleaving member can apply the force to the rock sample, the application being directed downwardly toward the work surface, substantially along the cleaving axis.

The rock trimmer, in accordance with one aspect of the invention, comprises a frame disposed above the rock sample, carried by one or more legs mounted on a platform. The first cleaving member comprises an upper cutter coupled to the frame. The positioning and hydraulic mechanisms are each operatively associated with the upper cutter by being operatively associated with the frame. That is, the positioning mechanism provides for retracting the upper cutter upwardly toward the frame so that the trimmer can receive a rock sample between the cutter and platform, and further provides for advancing the cutter downwardly toward the platform to a position adjacent to or engaging the rock sample. The hydraulic mechanism, in turn, provides for driving the upper cutter to cleave the sample into pieces. The platform preferably provides the work surface.

In accordance with other aspects of the invention, the positioning mechanism comprises an elongate member threaded through the frame. The threaded member has, at its proximal end, an actuator and, at its distal end, the upper cutter. The actuator preferably is disposed above the frame opposite the upper cutter and platform. The threaded member preferably has a thread pitch selected so that, when turned by the actuator, the member is advanced or retracted through the frame toward or away from the platform at a suitably rapid rate, while substantially maintaining positioning precision.

In accordance with still other aspects of the invention, the hydraulic mechanism comprises a hydraulic pump and a return bias mechanism, both of which are disposed in a bore formed along and through the longitude of the positioning mechanism's threaded member. The hydraulic pump has an actuator disposed at the proximal end of the member, above the frame opposite the platform. The upper cutter is mounted to one end of the return bias mechanism and is displaced to cleave the sample by operation of the actuator. After cleaving, the return bias mechanism returns the upper cutter to its undisplaced position.

In accordance with yet other aspects of the invention, the positioning and hydraulic mechanisms have a common actuator, the actuator preferably being manipulable so that each mechanism can be operated separately from the other mechanism and, at the same time, the operator can selectably perform either operation.

In accordance with further aspects of the invention, the positioning mechanism comprises devices other than the above-described single threaded member, including any one or more of a slide and lock assembly or a rack and pinion assembly. These devices operate to retract and advance the upper cutter relative to the work surface either (i) by adjusting the position of a member with which the upper cutter is operatively associated, or (ii) by raising and lowering the frame relative to the work surface. In raising and lowering the frame, the positioning mechanism either adjusts the position of the frame along the length of the legs or adjusts the length of the legs.

In accordance with still further aspects of the invention, the hydraulic mechanism produces cleaving forces and, to do so, displaces the frame toward or away from the work surface. This displacement, which is separate from any adjustment made by the positioning mechanism, drives the upper cutter toward or away from the rock sample. To displace the frame for cleaving-related purposes, the hydraulic mechanism either drives the frame along the length of the legs or adjusts the length of the legs.

In accordance with yet further aspects of the invention, the hydraulic and positioning mechanisms are both operatively associated with the upper cutter, but are isolated from one another.

As will be readily appreciated from the foregoing, the invention provides a manually-operated rock trimmer that overcomes the limitations of, and provides advantages over, conventional rock trimmers. For example: (i) using a positioning mechanism that does not effect cleaving, that is, using the mechanism solely to receive and engage the rock sample, means that the mechanism need not provide the mechanical advantage necessary to cleave and, therefore, allows having structure that provides relatively rapid, mechanically-efficient engagement and disengagement of rock samples; (ii) using a hydraulic mechanism provides for force multiplication; (iii) having positioning and hydraulic mechanisms in operative association with the frame (and, in particular, disposing their respective actuators above the frame) serves to optimize manual facility in operating the trimmer, to minimize the possibility of injury to the operator, to maximize operator leverage in operating the trimmer, and to minimize the opportunity for debris to enter the trimmer's mechanisms and degrade their performance; (iv) using an actuator common to the positioning and hydraulic mechanisms allows for selectable, single-handed operation of both mechanisms, and maximizes the operator's ability to counteract any undesirable moments experienced by the trimmer, while all the time maintaining grasp of and continuing to operate the trimmer; and (v) having a hydraulic mechanism disposed through the positioning mechanism accommodates a compact design that is relatively inexpensive to manufacture and easy to use. As a result, the invention includes all of the features and advantages of conventional rock trimmers, as well as adding additional features and advantages and overcoming disadvantages associated with conventional trimmers.

Accordingly, it is a principal object of the present invention to provide a novel and improved rock trimmer.

It is another object of the present invention to provide a novel and improved manually-operated rock trimmer employing hydraulics to cleave a rock sample into pieces.

It is a further object of the present invention to provide a rock trimmer that can be rapidly adjusted to receive a rock sample and that, once a rock sample is received, provides force multiplication in cleaving the sample.

It is yet another object of the present invention to provide a rock trimmer that is operated entirely from above the rock sample so as to optimize the manual facility of the trimmer's operation, to minimize the possibility of injury to the operator, and to maximize the operator's leverage in cleaving the rock sample.

It is yet a further object of the present invention to provide a rock trimmer that operators can use with only one hand, and without having to change hands, or to use two hands, or to release their grasp or otherwise substantially to change hand positions.

It is still another object of the present invention to provide a rock trimmer that is substantially stable during use, that minimizes undesirable use-related tilting and rotational moments, and that maximizes the operator's ability to counteract undesirable moments that the trimmer may experience, even while the operator all the time continues to operate the trimmer.

It is still a further object of the present invention to provide a rock trimmer having minimal free play between its cutting mechanisms and which substantially directs the cutting force downwardly toward the surface on which the trimmer is placed.

It is another object of the present invention to provide a rock trimmer that, in operation, is mechanically efficient.

It is a further object of the present invention to provide a rock trimmer that resists performance degradation by mechanical contamination relating to debris produced in cleaving rock samples.

It is yet another object of the present invention to provide a rock trimmer having an economy of structure and that is compact, durable and relatively lightweight.

It is yet a further object of the present invention to provide a rock trimmer that is simple in design, inexpensive to manufacture, and easy and substantially safe to use.

It is still another object of the present invention to provide a rock trimmer that can cleave variously sized rock samples.

It is still a further object of the present invention to provide a rock trimmer that is easily scalable in its dimensions.

It is another object of the present invention to provide a rock trimmer that can free-stand for use in the field, while also being mountable permanently or removably on a bench or other such structure, either in the home, office, laboratory or the like.

The foregoing and other objects, features and advantages of the invention will be more readily understood upon consideration of the following detailed description of the invention, taken in conjunction with the accompanying drawings.

DETAILED DESCRIPTION

Figure 1:
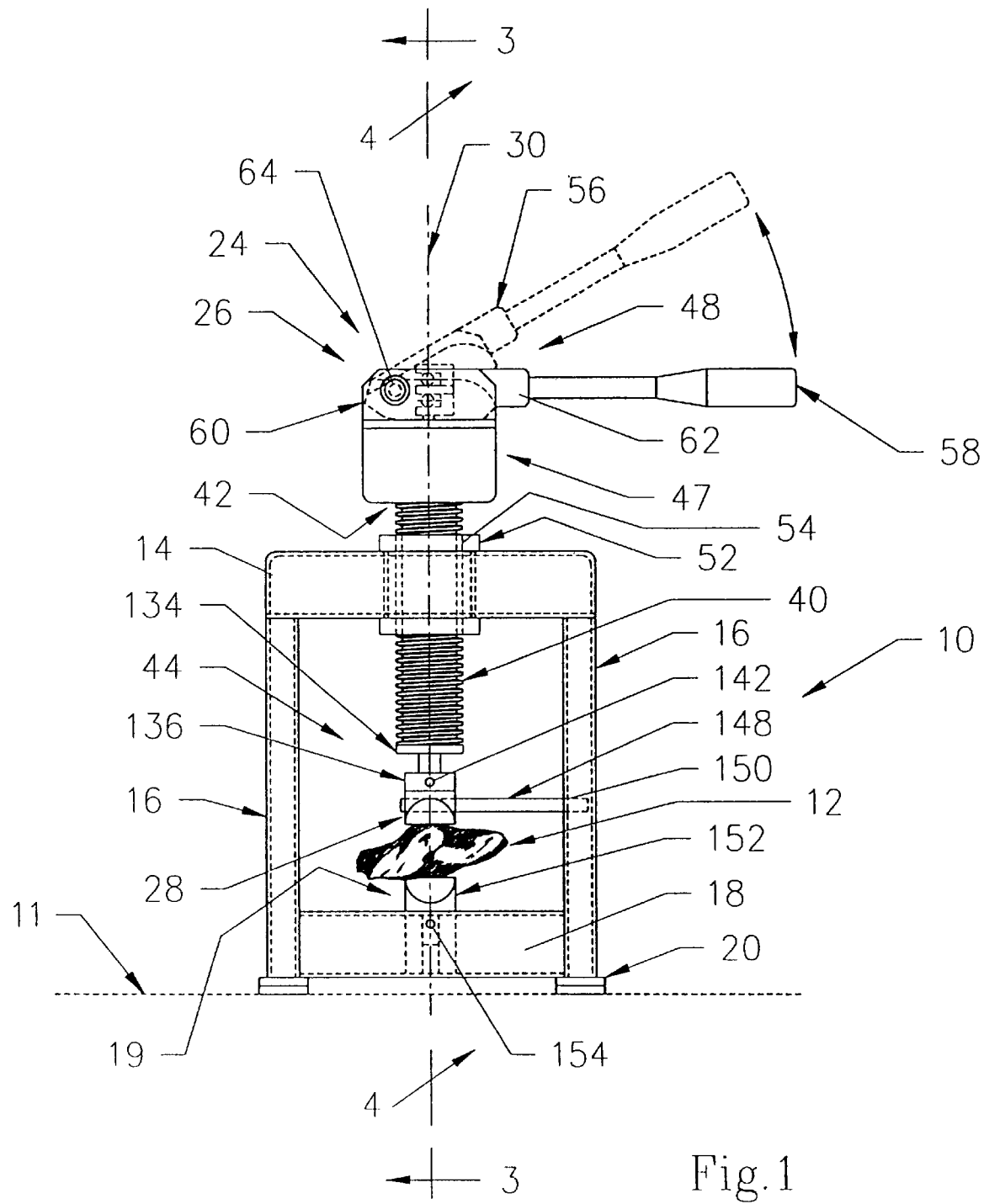
FIG. 1 is a front elevational view of a linear actuator in accordance with the present invention, implemented as a rock trimmer having a positioning mechanism and a hydraulic mechanism and the operation of the hydraulic mechanism being illustrated with respect to a rock sample received by the rock trimmer.
Figure 2:
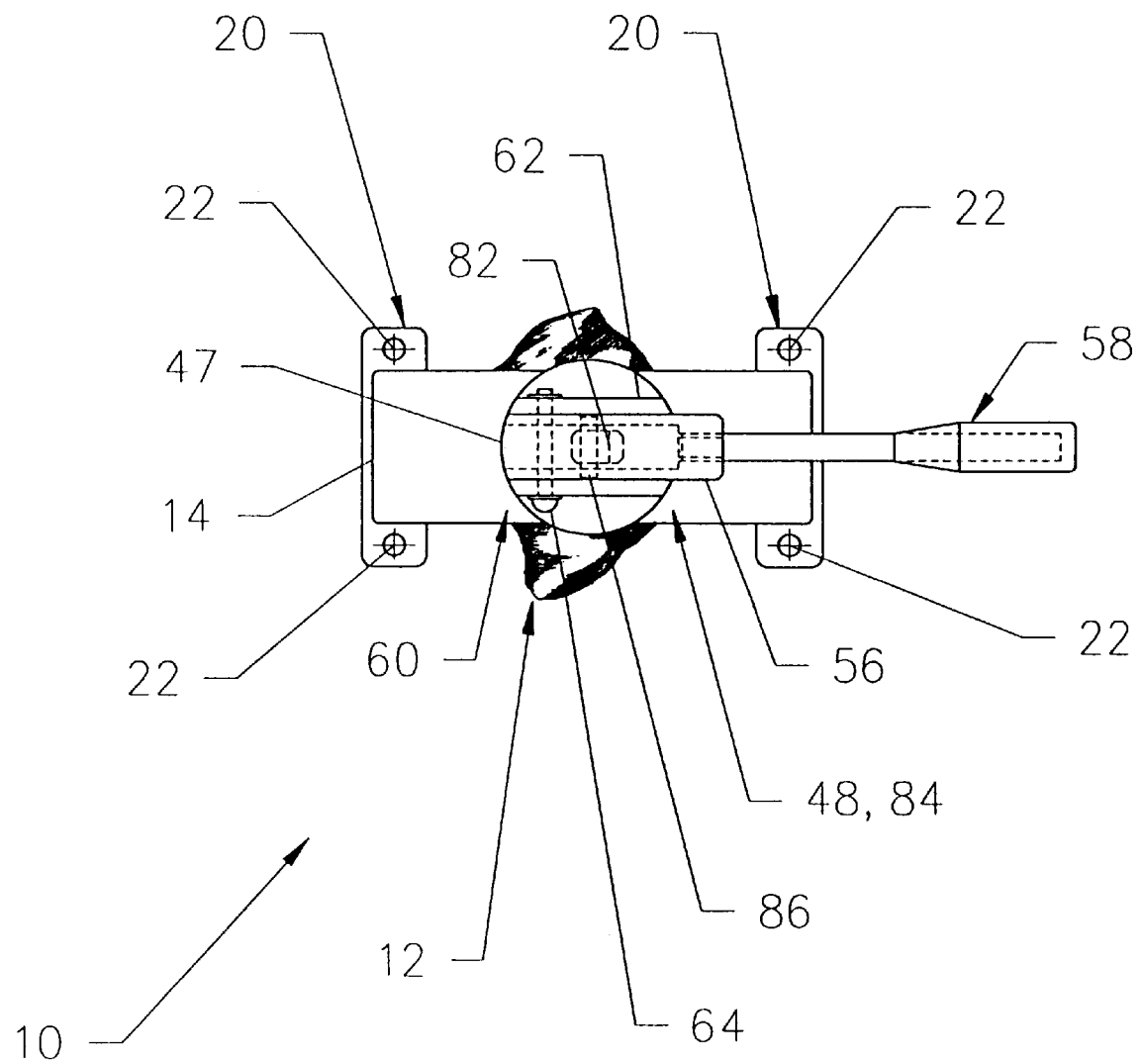
FIG. 2 is a top plan view of the rock trimmer of FIG. 1.
Figure 3:
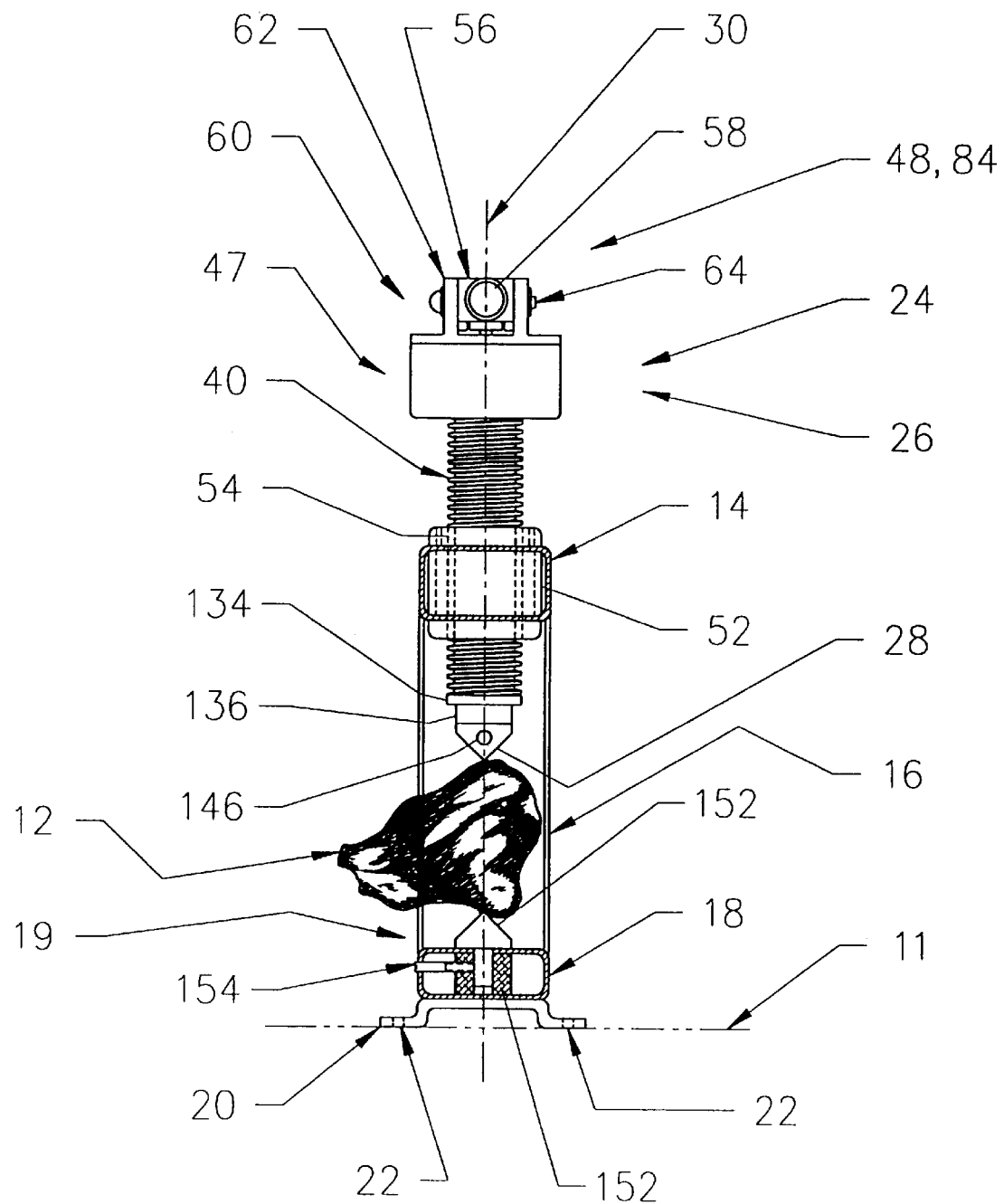
FIG. 3 is a partial cross-sectional view of the rock trimmer of FIG. 1, taken along line 3—3 thereof.

FIGS. 1, 2 and 3 illustrate a manually-operated rock trimmer 10 in accordance with the present invention, the rock trimmer 10 being illustrated together with a rock sample 12 positioned to be cleaved. The trimmer 10 is disposed on a support surface 11. For the purposes of this specification, it is to be understood that the term "rock" denotes rocks, stones, crystals, composites and other forms of mineral and organic matter, alone or in combination.

The rock trimmer 10 preferably comprises a frame 14 carried by opposed legs 16. The legs 16 in turn are mounted to a platform 18 so that the frame is disposed above the platform. So constructed, the rock sample 12 is received by the trimmer 10 between the frame 14 and the platform 18, the platform 18 providing a work surface 19 while also enhancing the trimmer's overall rigidity by interconnecting the legs 16. Although the frame 14, as shown, is carried by two legs 16, it is to be recognsized that the frame can be carried by other than two legs, including by one leg, without departing from the principles of the invention. It is also to be recognized that the rock trimmer 10 can be constructed and operated in the absence of the platform 18, without departing from the principles of the invention. In that case, the legs 16 are mounted on the support surface 11, and the rock sample 12 is received by the trimmer 10 between the frame 14 and the support surface 11, the support surface 11 thereby providing the work surface 19.

The rock trimmer 10 further comprises anchors 20. The anchors 20 are attached to and extend laterally from the platform 18 so as to provide stability. In particular, the anchors 20 enhance the ability of the trimmer 10 to free-stand on the support surface 11, particularly when used in the field. The anchors 20 have apertures 22 through which bolts or other fasteners are disposed so as to mount the trimmer 10, either permanently or removably, on the support surface 11, such as is provided by a bench or other such structure, in the home, office, laboratory or the like. It is to be recognized that the anchors 20 can be attached to respective legs 16 in conjunction with, or to the exclusion of, attachment to the platform 18, without departing from the principles of the invention.

The frame 14, legs 16 and platform 18 are shown constructed of metal tubing having substantially rectangular cross sections and having an exemplary gauge. It is to be recognized, however, that other materials and construction can be used without departing from the principles of the invention. That is, the tubing can be constructed of any suitable metal or alloy, including stainless steel or aluminum, or can be constructed of other materials, including plastics, fiberglass and carbon composites. In addition, the materials can be solid bars or hollow tubing and, particularly if tubing, can have cross-sectional shapes and gauges other than those shown, including shapes and gauges that are uniform or that vary. The important point is that the materials and construction are to be suitable for the intended application and, in particular, take into account various factors, including the maximum cleaving force likely to be applied by the trimmer 10 on the rock sample 12.

The frame 14, legs 16 and platform 18 preferably form a unitary structure. The unitary structure is achieved by welding, by casting or by using other techniques appropriate to the materials and construction employed. It is to be recognized, however, that the frame 14, legs 16 and platform 18 can form other than a unitary structure, without departing from the principles of the invention. For example, the frame 14 can, in some embodiments, be removably mounted on or slidably supported by one or more legs 16. Moreover, whether the frame 14 forms a unit with the legs 16, or not, the legs 16 can be removably mounted on the platform 18, such as by having apertures formed in the platform 20. In either non-unitary case, or otherwise, coupling mechanisms (such as detent devices) can be employed to secure together the separate parts, such as to secure the legs 16 in the platform's respective apertures. These alternative constructions accommodate disassembly of the trimmer 10, in particular to enhance portability.

The rock trimmer 10 includes a positioning mechanism 24 and a hydraulic mechanism 26, each mechanism 24 and 26 being operatively associated with an upper cutter 28. The upper cutter 28 is coupled to one or more of the legs 16, preferably by means of the frame 14. The upper cutter 28 has a cleaving axis 30, the axis 30 being directed through the rock sample 12 toward the work surface 19.

The positioning mechanism 24 provides for imparting rectilinear travel to the upper cutter 28 so as to selectively adjust its position relative to the work surface 19 and, therefore, the received rock sample 12, along the cleaving axis 30. More specifically, the positioning mechanism 24 provides for selectively retracting the upper cutter 28 upwardly away from the work surface 19 toward the frame 14 so that the trimmer 10 can receive the rock sample 12 below the cutter 28, and further provides for selectively advancing the upper cutter 28 downwardly away from the frame 14 toward the work surface 19 to a position adjacent to or engaging the rock sample 12. In this advanced position, the positioning mechanism 24 preferably can apply sufficient force so as to hold the rock sample 12 between the upper cutter 28 and the work surface 19. The positioning mechanism 24 preferably is constructed so as to be efficient in operation, in particular to provide for advancing and retracting the upper cutter 28 at a suitably rapid rate while substantially maintaining positioning precision above a selected threshold over the available range of travel.

The hydraulic mechanism 26 provides for driving the upper cutter 28 downwardly toward the work surface 19 so as to cleave the sample 12 into pieces. More specifically, the hydraulic mechanism 26 produces a force suitable for cleaving the sample 12. The cleaving force is transmitted from the hydraulic mechanism to the upper cutter 28 by a coupling mechanism 34, which will be described below with reference to FIG. 4. The upper cutter 28, in turn, applies that transmitted force to the rock sample 12, the application being directed downwardly substantially along the cleaving axis 30.

As is known in the art, the mechanism 26, by employing hydraulics, provides force multiplication to cleave the sample 12. That is, the force exerted by the operator in actuating the mechanism 26 is multiplied by hydraulic action so that a larger force is produced for application to the rock sample 12. Accordingly, the operator need exert only a relatively small force, thereby substantially freeing the trimmer 10 from dependency on operator strength in cleaving. Force multiplication also accrues other advantages to the trimmer 10, including minimizing operation-related tilting and rotational moments.

Hydraulic action provides force multiplication at the cost of reduced displacement. That is, a suitable cleaving force is produced at the upper cutter 28, but rectilinear travel of the upper cutter 28 generally is relatively slow. However, it is to be recognized, as previously described, that the positioning mechanism 24 preferably is constructed so as to provide a relatively rapid travel rate for the upper cutter 28. Accordingly, the positioning and hydraulic mechanisms 24 and 26 preferably are selected so as to have performance characteristics, such as travel rates and precision, that complement each other while being suitable for the trimmer's intended application.

Figure 4:
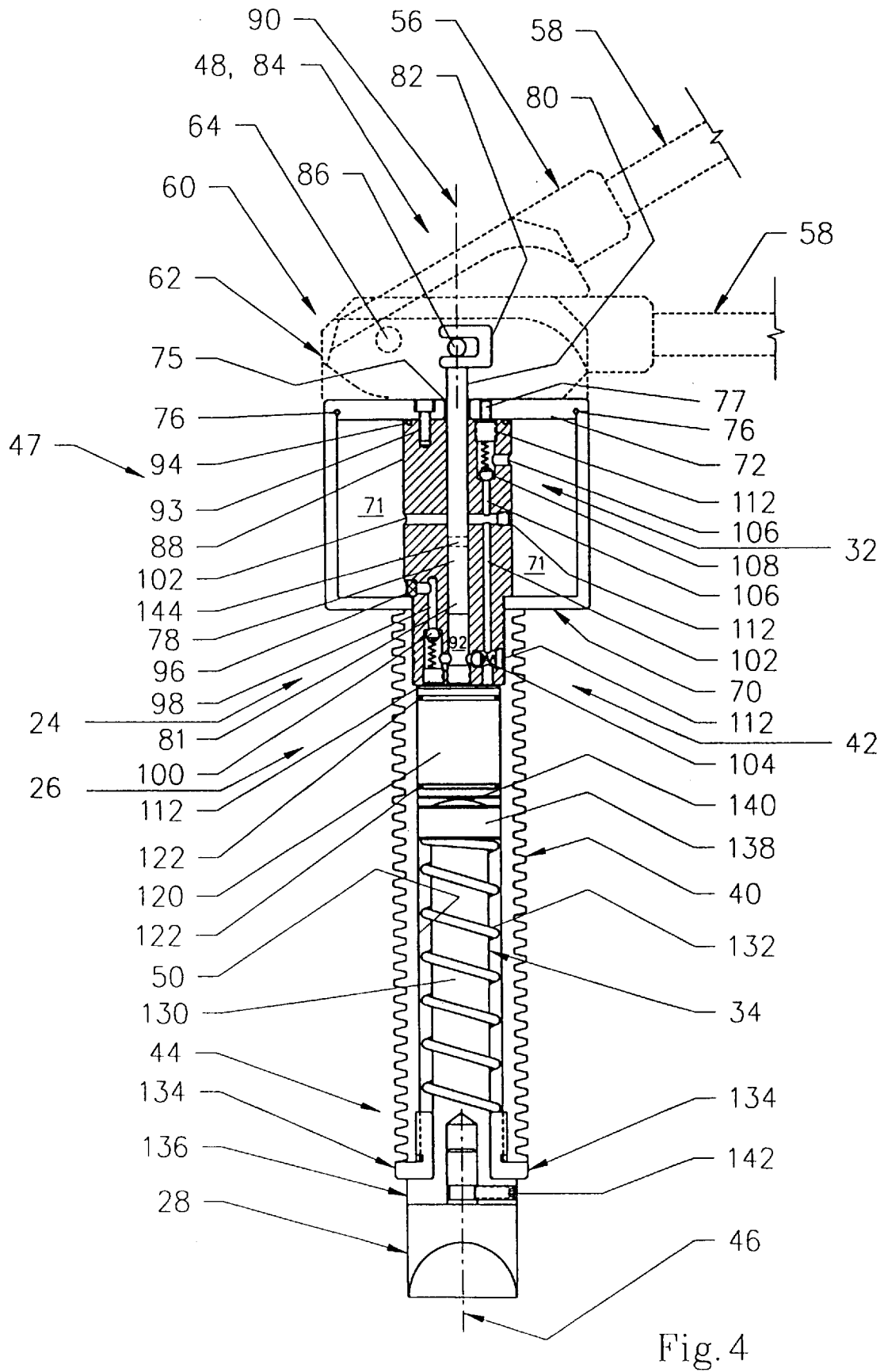
FIG. 4 is a partial cross-sectional view of the rock trimmer of FIG. 1, taken along line 4—4 thereof, showing in greater detail the structure of the positioning and hydraulic mechanisms.
Figure 5:
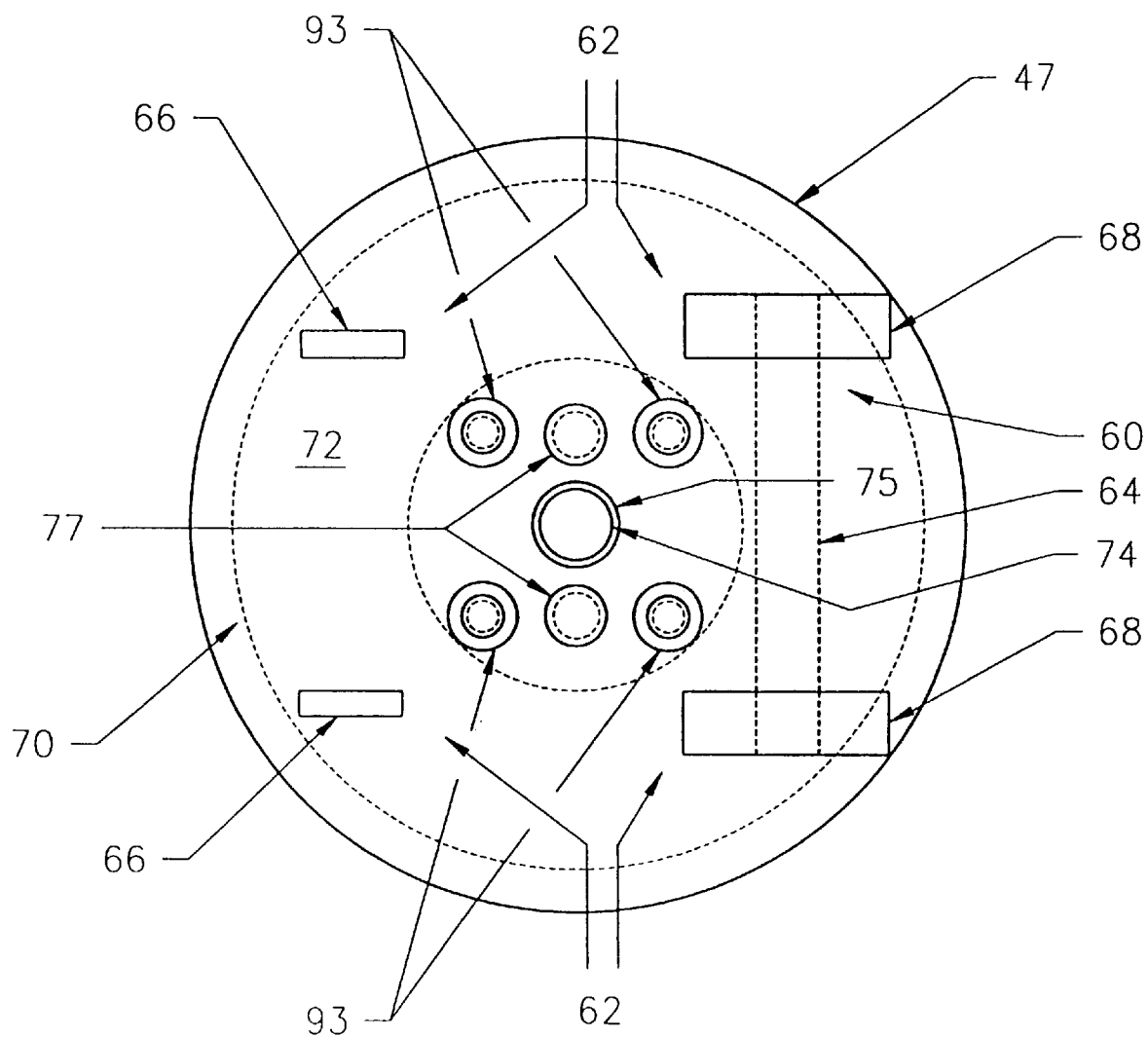
FIG. 5 is a top plan view of an alternative structure of a cover for use in the rock trimmer of FIG. 1.
Figure 6:
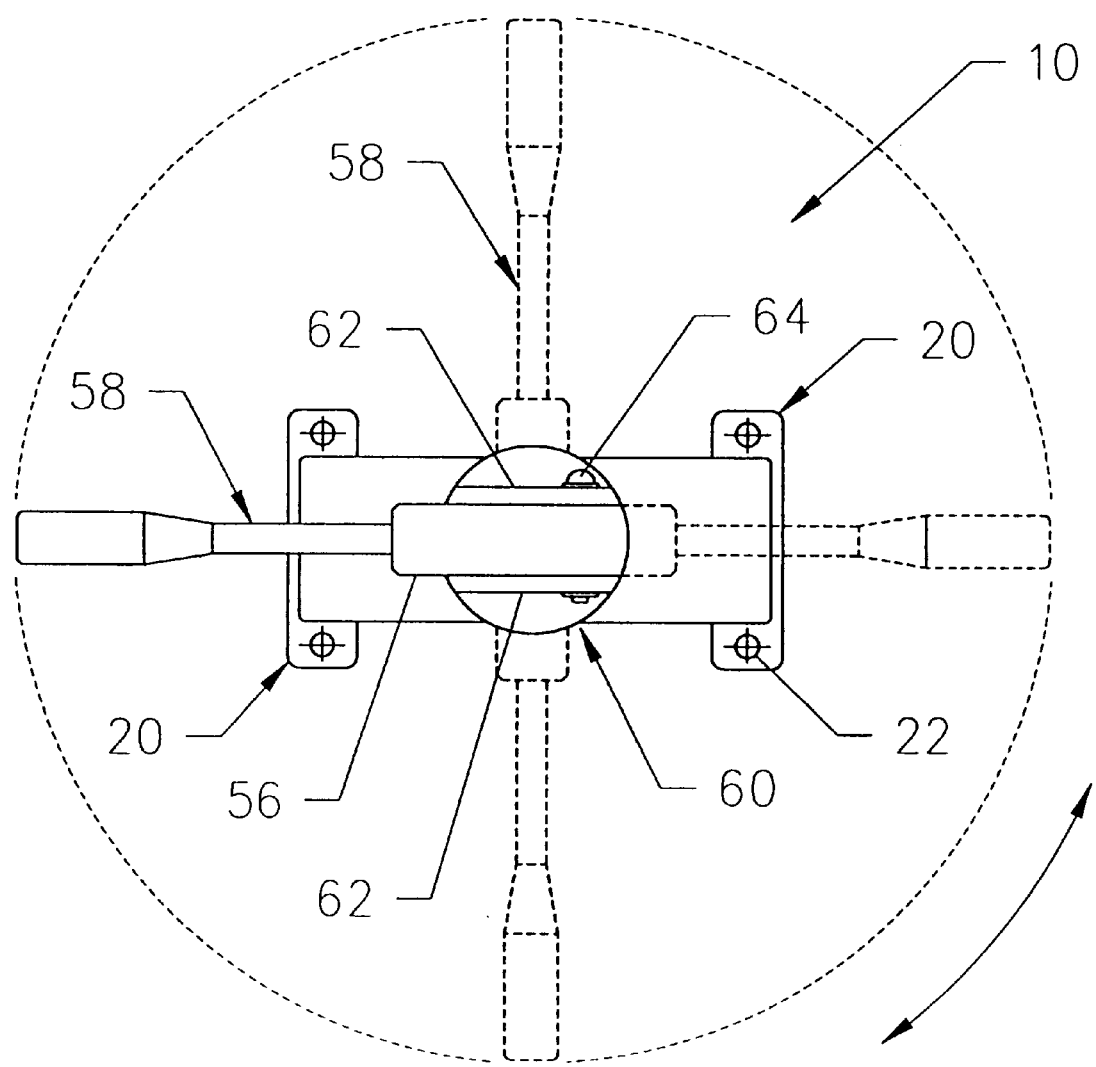
FIG. 6 is a top view of the rock trimmer of FIG. 1, illustrating operation of the positioning mechanism.

Referring now to FIGS. 4–6, as well as to FIGS. 1–3, greater detail is shown of one embodiment of the positioning and hydraulic mechanisms 24 and 26. In this embodiment, the positioning mechanism 24 comprises an elongate member 40 having a proximal end 42, a distal end 44 and longitudinal axis 46. At its proximal end 42, the elongate member 40 has a head 47 beyond which extends a positioning actuator 48. At its distal end 44, the elongate member 40 has the upper cutter 28. The elongate member also has a bore 50 disposed from the proximal end 42 through the distal end 44, so as to be substantially aligned with the longitudinal axis 46. The bore 50 preferably is substantially cylindrical, but can have other dimensions and cross-sectional shapes, without departing from the principles of the invention.

Referring particularly to FIGS. 1 and 3, the elongate member 40 is coupled to the legs 16 by means of the frame 14. Coupling preferably is achieved by threading the member 40 into and through a mounting collar 52 disposed through the frame 14, the frame 14 being carried by the legs 16. The collar 52 has a threaded interior aperture 54 for receiving the member's threads.

Referring particularly to FIGS. 1–5, the positioning actuator 48 comprises a lever 56 comprising a handle 58 and a pivot 60, the lever 56 being rotatable as respects the head 47. The handle 58 preferably is removably attached to the lever 56, secured thereon using a spring-loaded detent device or otherwise. The pivot 60 is formed by one or more flanges 62 and a pin 64 disposed between the flanges, the lever 56 being pivotally mounted to the pivot 60 by the pin 64. The flanges 62 extend upwardly from the head 47 and have selected shapes and dimensions: the flanges 62 can reach fully across the head 47 as shown in FIG. 1, or can be divided as shown in FIG. 5, including to form relatively short, narrow portions 66 and relatively tall, thicker portions 68. It is to be recognized that the flanges 62 can have still other shapes and dimensions without departing from the principles of the invention. The important point is that the flanges 62 are suitable for formation of the pivot 60 and for reception of the pin 64, while also providing the structure for diverting actuation forces applied to the positioning actuator 48 so as to protect the relatively less sturdy pin 64, as well as other elements associated with the head 47.

In operation, as shown particularly in FIGS. 1 and 6, the handle 58 preferably is manipulated so that the lever 56 pivots to a position substantially flush with the top of the head 47, whereby the lever 56 engages the flanges 62. To actuate the positioning mechanism 24, the handle 58 is rotated about the longitudinal axis 46 of the elongate member 40, in either a clockwise or a counterclockwise direction, as indicated by the two-headed arrow of FIG. 6. By rotating the handle 58 in one direction, the elongate member 40 is retracted through the frame 14 away from the work surface 19 so that the trimmer 10 can receive the rock sample 12. By turning the handle 58 in the other direction, the elongate member 40 is advanced downwardly toward the work surface 19 so that the upper cutter 28 (disposed at the member's distal end 44) is positioned adjacent to or engaging the received rock sample 12. With the upper cutter 28 so positioned, the hydraulic mechanism 26 is then actuated to drive the upper cutter 28 to cleave the sample 12 into pieces, as described below.

The elongate member 40 preferably is constructed of metal and has a cross-sectional thickness suitable for the trimmer's intended application. It is to be recognized that the member 40 may be formed of materials other than metal and may have construction other than that shown in the Figures, without departing from the principles of the invention; the important point being that the materials and construction take into account various factors, including the maximum cleaving force to be applied by the trimmer 10 on the rock sample 12.

The elongate member 40 preferably has thread pitch selected so that, when the handle 58 is rotated, the member 40 is advanced or retracted through the frame 14 toward or away from the work surface 19 at a suitably rapid rate. At the same time, the member's thread pitch is selected so that the upper cutter 28 can be positioned, with suitable precision, adjacent to or engaging the rock sample 12, particularly in light of and to complement the performance characteristics of the hydraulic mechanism 26.

The hydraulic mechanism 26 preferably comprises a hydraulic pump 32 and a coupling mechanism 34. The general principles of operation of the pump 32 are known in the art. Referring particularly to FIG. 3, the hydraulic pump 32 includes a fluid reservoir 70, hydraulic fluid 71, a reservoir cover 72, and gaskets 76. The gaskets are used to form a fluid-tight seal between the reservoir 70 and cover 72. The cover 72 preferably is removable form the reservoir 70 using a puller 77. The cover 72 has a centrally disposed accessway 74 therethrough, as is described further below. The cover 72 and reservoir 70 substantially define the head 47, described above with respect to the elongate member 40. The hydraulic fluid 71 employed in the mechanism 26 preferably is any high-quality, substantially incompressible liquid, including water, oils or other fluids, particularly those specifically manufactured for hydraulic uses. It is to be recognized, however, that in some applications gasses, particularly compressed gasses, may be adequate for use, notwithstanding their generally relatively higher compressibility.

The hydraulic pump 32 also includes a first piston 78 having a proximal end 80 and a distal end 81. A seating member 82 is disposed at the piston's proximal end 80 and is coupled to a cleaving actuator 84 by means of an engagement pin 86 mounted to the actuator. The seating member 82 and the cleaving actuator 84, including the engagement pin 86, are disposed beyond the head 47, opposite the elongate member 40. The cleaving actuation 84, except for the engagement pin 86, shares with the positioning actuation 48 the lever 56 and other elements described above. More specifically, the engagement pin 86 is mounted to the lever 56 and rides in the seating member 82. The cleaving actuator 84 actuates the hydraulic pump 32 by pivoting about the pivot 60, up and down in an arc, as indicated by the two-headed arrow of FIG. 1. The pivoting is induced by the operator applying pumping action to the handle 58. The pivoting causes the first piston 78 to move reciprocally, being translated to linear motion by the pin 86 riding in the seating member 82. Riding in the member 82, the pin 86 preferably has sufficient free-play so that forces and torques that are out of alignment with the pumping are not translated to the first piston 78, thereby protecting the piston 78 from damage.

The hydraulic pump 32 further comprises an elongate cylinder block 88 having a longitudinal axis 90, as well as an aperture 92 disposed through the block in substantial alignment with the axis 90. The cylinder block 88 is mounted substantially centrally through the reservoir 70 so as, at one end, to receive one or more fasteners 93 that secure the cover 72 to the block, while drawing the cover 72 against the reservoir 70 to seat the gaskets 76. The cylinder block 88 has associated gaskets 94 disposed between the block and the cover 72 so as to create a fluid-tight seal therebetween. The cylinder block 88, at its other end, is mounted to the proximal end 42 of the elongate member 40, such as by threading one into the other or by any other appropriate method. In so mounting the cylinder block 88, the block's longitudinal axis 90 preferably is collinear with the longitudinal axis 46 of the elongate member 40. In addition, the block's aperture 92 is substantially aligned with the accessway 74 of the cover 72.

The first piston 78 is slidably disposed in the cylinder block's aperture 92, with the proximal end 80 extending through the cover's accessway 74. The first piston 78 and aperture 92 preferably are manufactured so as conform to a high tolerance, particularly so that hydraulic fluid 71 properly drawn into the aperture 92 is prevented from escaping past the piston-aperture interface. The cover's accessway 74 has a seal 75 both to further prevent any such escape and to substantially resist entry of contamination into the hydraulic mechanism 26. The seal 75 preferably is made of nylon.

The cylinder block 88 further comprises a filter 96, intake ducting 98, an intake valve 100, exhaust ducting 102, an exhaust valve 104, safety ducting 106, a safety valve 108, bore access ducting 110 and a plurality of seals 112. The seals 110 make fluid-tight the various valves, as well as the aperture 92 as respects the bore 50, so that, in addition to resisting undesirable leaks, the hydraulic fluid 71 is directed to flow from, to and among the various valves, ducting and other elements as appropriate to the pump's operation. For example, when the first piston 78 is pulled from the cylinder block 88 out the accessway 74, hydraulic fluid 71 is drawn from the reservoir 70 into the aperture 92, the fluid flowing in turn through the filter 96, intake ducting 98 and intake valve 100. In this operation, hydraulic fluid 71 in the bore 50 is prevented from backing up into the aperture 92 because, in that circumstance, the exhaust valve 104 closes off access. The fluid 71 is also prevented from reentering the reservoir 70 both because the safety valve 108 closes off the safety ducting 106, and because the first piston 78 blocks the exhaust ducting 102.

In another example, when a withdrawn first piston 78 is pushed back into the block 88, fluid 71 in the aperture 92 is forced out by the first piston's distal end 81, the fluid flowing in turn through the exhaust valve 104 and bore access ducting 110 into the bore 50 of the elongate member 40. In this operation, the hydraulic fluid 71 is prevented from returning to the reservoir 70 through the intake ducting 98 by the closing action of the intake valve 100, as well as by action of the safety valve 108 and first piston 78 as previously described. However, if pushing the first piston 78 increases the pressure of the fluid 71 in the bore 50 so as to reach the pressure rating of the safety valve 108, the valve 108 will open to release fluid back into the reservoir 70 through the safety ducting 106, thereby imposing a limitation on the cleaving force that can be generated by the trimmer 10. The safety valve 108 preferably is selected by its pressure rating, taking into account various factors, including the maximum cleaving force intended for the trimmer 10 to generate and the materials, construction, dimensions and other characteristics of the trimmer's structure.

The hydraulic pump 32 further comprises a main piston 120 slidably disposed in the bore 50 of the elongate member 40. The main piston 120 preferably is manufactured to a high tolerance so as to substantially conform to the dimensions of the bore 50. The main piston 120 also comprises gaskets 122 disposed around its periphery so as to form a fluid-tight seal against the bore 50. The main piston 120 has a selectable length dimension along the longitudinal axis 42 of the elongate member 40, that length preferably being selected to optimize performance of the pump 32 by considering factors including a determination of a suitable amount of friction between the bore 50 and the main piston 120, in particular to maximize mechanical efficiency while accommodating any effects thereof on the proper operation of the coupling mechanism 34.

The coupling mechanism 34 comprises a connector 130 slidably disposed in the bore 50 of the elongate member 40. The coupling mechanism 34 further comprises a compression spring 132 disposed in the bore 50 around the connector 130, a retainer 134 mounted to the elongate member 40 at the member's distal end 44, and a cutter flange 136 extending outside the member's distal end 44 and being attached to the connector 130 adjacent the retainer 134. The coupling mechanism 34 also comprises a slide block 138 mounted to the end of the connector 130 adjacent the main piston 120, as well as a head 140 for engaging the main piston 120. The slide block 138 preferably has a cross-sectional shape and dimensions conforming to those of the bore 50. However, it is not necessary that the conformity be to a high tolerance. Because the conformity may be to a low tolerance, the head 140 preferably is rounded so as to properly engage the main piston 120 regardless of any lateral free-play between the slide block 138 and bore 50 in operation. In addition, the retainer 134 serves to guide the connector 130.

The compression spring 132 is retained between the retainer 134 and the slide block 138. When compressed by displacement of the main piston 120 toward the member's distal end 44, the spring 132 applies an urging force to the slide block 138 that is directed toward the member's proximal end 42. The compression spring 132 preferably is selected, among other factors, so as to provide an urging force that is readily overcome by the force generated by the hydraulic pump 32, and that is also suitable to overcome the friction between the main piston 120 and the bore 50 when the pump's force is removed, as described below. The spring's urging force also maintains the head 140 in engagement with the main piston 120, regardless of the displacement of the coupling mechanism 34.

The cutter flange 136 provides for rotatable mounting of the upper cutter 28 to the coupling mechanism 34. A set screw 142 is employed for holding the mounted cutter.

In operation, when hydraulic fluid 71 is pumped by the first piston 78 into the bore 50 between the cylinder block 88 and the main piston 120, the main piston 120 is displaced toward the distal end 44 of the elongate member 40, as described above, to produce a cleaving force. The cleaving force is transmitted to the upper cutter 28 through the connector 130 which engages the main piston 120 by means of head 140. After cleaving is complete, the operator manipulates the hydraulic pump 32 to exhaust the fluid 71 from the bore 50 under the urging force applied by the spring 132 on the main piston 120. That is, the coupling mechanism 34 establishes pressure gradient between the bore 50 and the reservoir 70, so that the fluid is forced from the bore 50 back into the reservoir 70. In turn, the main piston 120 is retracted back toward the proximal end 42 of the elongate member 40, particularly toward an undisplaced position adjacent the cylinder block 88.

When exhausting fluid from the bore 50, so as to allow the fluid 71 to flow to the reservoir 70 through the exhaust ducting 108, the first piston 78 preferably has a port 144 disposed laterally therethrough. More specifically, the port 144 is formed so that, using a predetermined manipulation of the cleaving actuator 84, the port 144 aligns with and opens the exhaust ducting 102 for fluid flow. As shown, the predetermined manipulation is to pivot the lever 56 so as to pull the first piston 78 to or near its outermost position. It is to be recognized, however, that other structure, or other manipulations, or both, may be used to trigger exhaust of fluid from the bore 50, each without departing from the principles of the invention.

As shown in the Figures, the positioning actuator 48 and the cleaving actuator 84 comprise a substantially common mechanism. The actuators 48 and 84 are both manipulable by the handle 58. Handle rotation operates the positioning mechanism 24, while handle pivoting operates the hydraulic mechanism 26.

The upper cutter 28 preferably has an aperture 146 for selectively receiving one end of an alignment arm 148. The other end of the alignment arm 148 is received in a guideway 150 provided in one of the legs 16. The alignment arm 148 can be used at the discretion of the operator to hold the rotatable upper cutter 28 in the alignment given by the arm. For example, the alignment can comport with the orientation of a lower cutter 152. The lower cutter 152 preferably is removably mounted on the platform 18 and secured thereon using a set screw 154. It is also to be recognized that the upper and lower cutter's 28 and 152 can be of various types, shapes and materials, and combinations thereof, without departing from the principles of the invention.

The rock trimmer 10 preferably includes legs 16 of a fixed length and a frame 14 carried at a fixed location along the legs 16, while having positioning and hydraulic mechanisms 24 and 26 that are disposed for operation substantially midway along the frame 14 and that are substantially integrated with one another. It is to be recognized, however, that the rock trimmer 10 can have legs 16 of adjustable length, can have a frame 14 that is adjustably positionable along the legs 16, can have mechanisms 24 and 26 that are disposed other than midway along the frame 14 or that are not substantially integrated, or can have combinations of any two or more of these, all without departing from the principles of the invention.

For example, if the frame's position along a leg 16 is adjustable, either or both the positioning mechanism 24 and the hydraulic mechanism 26 can be disposed on the trimmer 10 so as to control the frame's location relative to the leg 16. Where the positioning mechanism 24 so controls the frame 14, the mechanism 24 can comprise a threaded member, as described above. However, it is to be understood that other structure can be used, including rack and pinion or slide and lock assemblies, without departing from the principles of the invention. In turn, where the hydraulic mechanism 26 so controls the frame 14, the mechanism 26 can be mounted on trimmer 10, including on a leg 16, above and engaging the frame 14, so as to displace the frame 14 up and down and, thereby, to transmit cleaving force to the upper cutter 28. In that case, the upper cutter 28 is not mounted directly to the hydraulic mechanism 26, but rather is mounted either (i) to the positioning mechanism 24 which is coupled midway along the frame 14 as described above, or (ii) directly to the frame 14, particularly if the mechanism 24 adjusts the cutter's position by adjusting the frame's location along the legs 16. In each case, any mechanism 24 or 26 not operating by adjusting the frame's location, can operate by adjusting the length of one or more legs 16. In yet another case, both mechanisms 24 and 26 can operate by adjusting leg length.

Depending on the mechanical connection between the respective positioning and hydraulic mechanisms 24 and 26, on the one part, and the legs 16 and the frame 14, on the other part, the mechanisms 24 and 26 may or may not be integrated as previously described (or in any other way), and can be entirely separate from one another, without departing from the principles of the invention. However, in each case, the upper cutter 28 preferably has rectilinear travel along the cleaving axis 30 based on the positioning mechanism's operation, and has cleaving force transmitted thereto from the hydraulic mechanism 26 for application directed downwardly toward the work surface 19 substantially along the cleaving axis 30.

Figure 7:
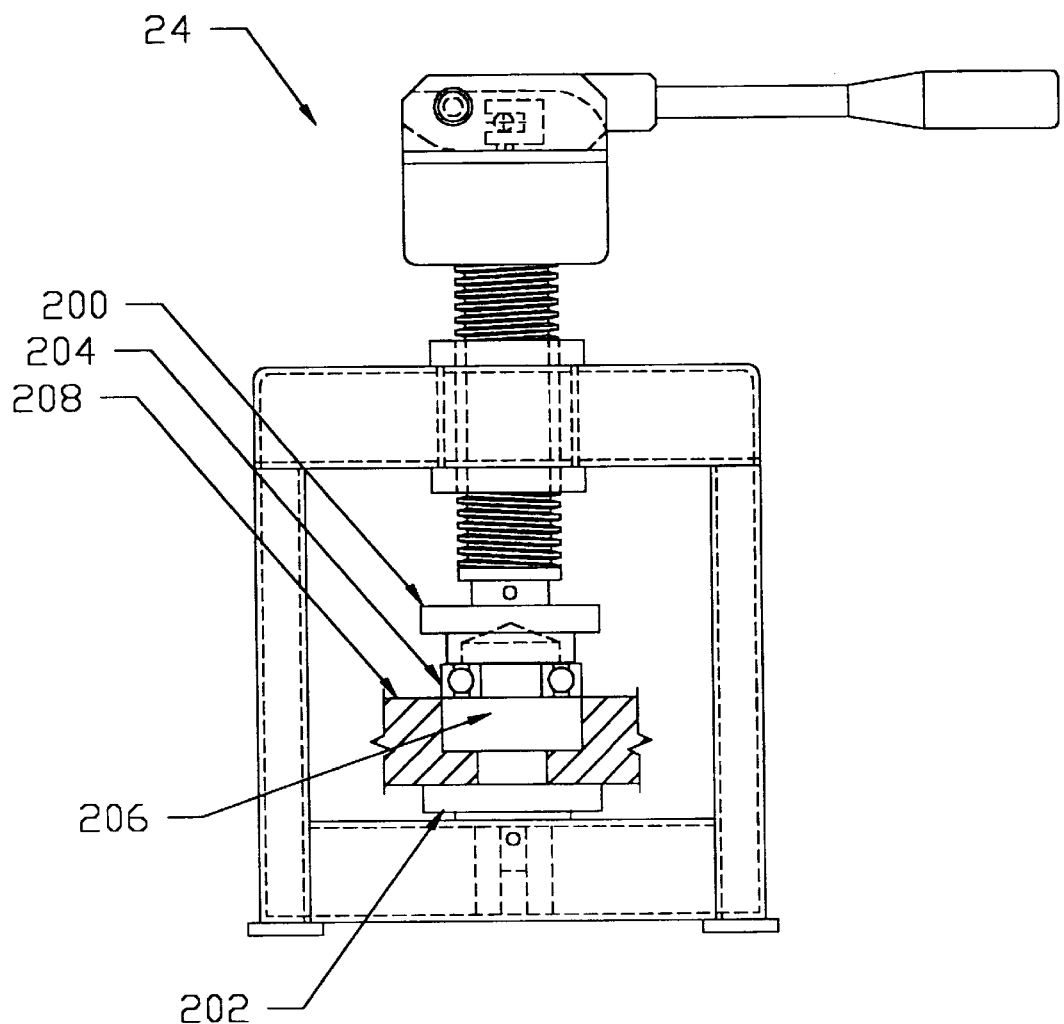
FIG. 7 is a front elevational view of a second linear actuator in accordance with the present invention.

It will be appreciated that the linear actuator described above is not restricted in its application to a rock trimmer and may be used in other applications where a force must be applied to a workpiece. For example, as shown in FIG. 7 the upper cutter 28 and the lower cutter 152 may be replaced with a pressing tool 200 and a support table 202, and the linear actuator can then be used for pressing a ball bearing 204 into a recess 206 in a bearing housing 208. The positioning mechanism 24 is used to adjust the position of the pressing tool 200 to allow the ball bearing to be placed over the recess in the bearing housing, and to advance the pressing tool to a position adjacent to or engaging the outer race of the ball bearing. The hydraulic mechanism is then used to force the pressing tool toward the support table and force the ball bearing 204 into the recess 206. Another possible application of the linear actuator is in a cutting device for stamping out pieces from a sheet of tough material. In this case, the upper and lower cutters 28 and 152 may be replaced with the punch and die that define the outline of the desired pieces. Yet other possible applications of the linear actuator are in pressure molding a plastically deformable material or in compressing or bending a workpiece.

The linear actuator may also be used to apply a pulling force, for example for removing press fitted or heat fitted parts such as gears or pulleys from a shaft.

Figure 8:
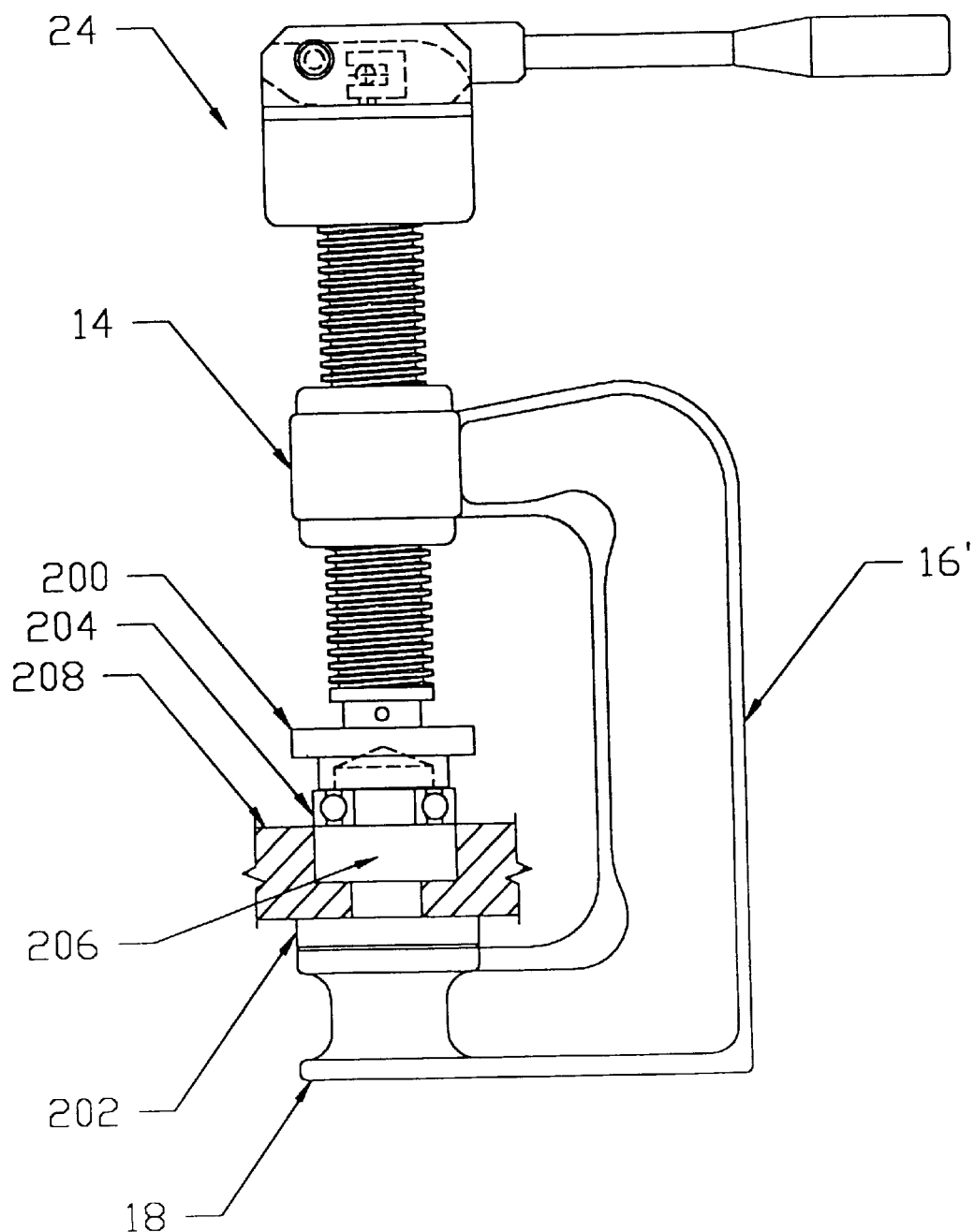
FIG. 8 is a front elevational view of a third linear actuator in accordance with the present invention.

FIG. 8 illustrates a third linear actuator in accordance with the present invention, wherein the frame 14 is supported relative to the platform 18 by only one leg 16'.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A linear actuator for applying a force to a tool, the linear actuator comprising:
    a support member;
    a tool holder coupled to said support member;
    a positioning mechanism, operatively associated with said tool holder, for imparting rectilinear travel to said tool holder along a working axis;
    a hydraulic mechanism for producing a working force in a first direction along said working axis;
    a force transmission mechanism operatively associated with said tool holder so as to transmit said working force to said tool holder; and
    a frame carried at a fixed location along said support member, at least one of said positioning and hydraulic mechanisms being disposed on said frame,
    and wherein:
        said positioning mechanism comprises a threaded member having a longitudinal axis, a proximal end and a distal end, said longitudinal axis being substantially collinear with said working axis, said member being threaded through said frame, and said rectilinear travel being imparted by rotating said threaded member,
    said force transmission mechanism comprises a biasing mechanism producing an urging force in a second direction, opposite said first direction, along said working axis so that, when said working force is removed, said biasing mechanism moves said tool holder in the direction of said urging force, and
    said hydraulic mechanism comprises a hydraulic fluid reservoir, a cylinder block, a first piston, exhaust ducting, a main piston and a main piston cylinder, said cylinder block having a longitudinal aperture therethrough, said first piston slidably disposed in said aperture and having a port disposed laterally therethrough, said main piston being disposed in said main piston cylinder and said exhaust ducting connecting said main piston cylinder to one side of said longitudinal aperture of said cylinder block and from the other side of said longitudinal aperture to said hydraulic fluid reservoir, said first piston being positionable to align said port with said exhaust ducting so as to make fluid connection across said longitudinal aperture, whereby when said biasing mechanism moves said tool holder in the direction of said urging force, hydraulic fluid disposed in said main piston cylinder flows back to the hydraulic fluid reservoir through said port.

2. A linear actuator according to claim 1, wherein said threaded member has a bore formed substantially along said longitudinal axis of said member, said bore comprising said main piston cylinder.

3. A linear actuator according to claim 2, wherein said biasing mechanism includes a return biasing member disposed movably within said bore.

4. A linear actuator according to claim 1, comprising an actuating member coupled to said first piston for reciprocatingly moving said first piston in said longitudinal aperture.

5. A linear actuator according to claim 4, wherein said actuating member is coupled to said threaded member for effecting rotation of said threaded member relative to said frame.

6. A linear actuator for applying a force to a tool, the linear actuator comprising:
    a support member;
    a positioning mechanism mounted to the support member for linear movement relative thereto along a working axis;
    a tool holder operatively associated with the positioning mechanism, whereby the tool holder is coupled to the support member and rectilinear travel alone the working axis relative to the support member is imparted to the tool holder by the positioning mechanism; and
    a hydraulic mechanism producing a working force along said working axis, said hydraulic mechanism being operatively associated with said tool holder so as to transmit said working force to said tool holder,
    and wherein:
        said hydraulic mechanism comprises a hydraulic pump and a main piston housed in a main piston cylinder,
        said positioning mechanism comprises an elongate member having a bore formed along the longitudinal axis of said elongate member, said bore comprising said main piston cylinder, and said hydraulic pump is attached to the elongate member and moveable relative to the support member with the elongate member.

7. A linear actuator according to claim 6, comprising a force transmission mechanism operatively associated with said tool holder so as to transmit the force generated by the main piston to the tool holder.

8. A linear actuator according to claim 6, wherein the hydraulic pump comprises a cylinder block having a longitudinal aperture therethrough, and a first piston slidably disposed in said aperture and substantially collinear with the main piston.

9. A linear actuator for applying a force to a tool, the linear actuator comprising:

a support member;

a positioning mechanism mounted to the support member for linear movement relative thereto along a working axis;

a tool holder operatively associated with the positioning mechanism, whereby the tool holder is coupled to the support member and rectilinear travel along the working axis relative to the support member is imparted to the tool holder by the positioning mechanism;

a hydraulic mechanism producing a working force along said working axis in a first direction; and a force transmission mechanism operatively associated with said tool holder so as to transmit said working force to said tool holder, and wherein:

said hydraulic mechanism comprises a hydraulic pump that produces said working force, said tool holder is mounted to said force transmission mechanism, said force transmission mechanism transmits said working force to said tool holder so as to displace said tool holder, said force transmission mechanism comprises a biasing mechanism producing an urging force along said working axis in a second direction, opposite said first direction, so that, when said working force is removed, said biasing mechanism moves said tool holder in the direction of said urging force, said positioning mechanism comprises an elongate member having a longitudinal axis and a bore formed substantially along said longitudinal axis, said hydraulic pump is attached to the elongate member and moveable relative to the support member with the elongate member, and said biasing mechanism includes a member disposed movably within said bore.

10. A linear actuator for applying a force to a tool, the linear actuator comprising:

a support member;

a tool holder coupled to said support member;

a positioning mechanism, operatively associated with said tool holder, for imparting rectilinear travel to said tool holder along a working axis; and a hydraulic mechanism producing a working force along said working axis, said hydraulic mechanism being operatively associated with said tool holder so as to transmit said working force to said tool holder, and wherein:

said positioning and hydraulic mechanisms have a common actuator, said actuator being manipulable so that each said mechanism can be operated separately from the other said mechanism and, at the same time, said operations can be selectably performed.

11. A linear actuator for applying a force to a tool, the linear actuator comprising:

a support member;

a frame member carried by said support member;

an elongate positioning member having a central axis, said positioning member being engaged with said frame member and having a first end and a second end, the positioning member being moveable relative to the frame member along said central axis;

a receiving means for receiving the tool, said receiving means being in abutting relationship with the first end of the positioning member, whereby movement of the positioning member in one direction along said central axis is accompanied by movement of the receiving means, and the receiving means being moveable in said one direction relative to the positioning member; and a hydraulic press including a hydraulic pump and a main piston which is moveable relative to the positioning member and is operatively associated with said hydraulic pump for producing a working force directed substantially in said one direction, said main piston being operatively associated with said receiving means so as to advance said receiving means substantially in said one direction relative to the positioning member and transmit said working force to said receiving means, and wherein the positioning member defines a central bore, the receiving means is slidably fitted in the central bore at the first end of the positioning member, the main piston is fitted in the central bore of the positioning member between the receiving means and the second end of the positioning member and is in engagement with the receiving means, and the receiving means is moveable in the central bore relative to the main piston in a direction transverse to said central axis.

12. A linear actuator according to claim 11, further comprising a biasing mechanism biasing the receiving means toward the main piston.

13. A linear actuator according to claim 11, wherein the positioning member is in threaded engagement with the frame member.

14. A linear actuator according to claim 11, further comprising an actuating member moveable in at least first and second degrees of freedom and in operative engagement with both the positioning member and the hydraulic press, and the positioning member being responsive to movement of the actuating member in said first degree of freedom and the hydraulic press being responsive to movement of the actuating member in said second degree of freedom.

15. A linear actuator according to claim 11, wherein the hydraulic pump includes a pump body and a pump piston fitted slidably in a bore in the pump body, and wherein the pump body is attached to the positioning member so that movement of the positioning member relative to the frame member is accompanied by movement of the pump body relative to the frame member.

16. A linear actuator for applying force to a tool, the linear actuator comprising:

a support member;

a frame member carried by said support member;

an elongate positioning member having a central axis, said positioning member being engaged with said frame member and having a first end and a second end, the positioning member being moveable relative to the frame member along said central axis;

a receiving means for receiving the tool, said receiving means being in abutting relationship with the first end of the positioning member, whereby movement of the positioning member in one direction along said central axis is accompanied by movement of the receiving means in said one direction, and the receiving means being moveable in said one direction relative to the positioning member;

a hydraulic press including a hydraulic pump and a main piston which is moveable relative to the positioning member and is operatively associated with said hydraulic pump for producing a working force directed substantially along said central axis in said one direction, said main piston being operatively associated with said receiving means so as to advance said receiving means in said one direction relative to the positioning member and transmit said working force to said receiving means for application by the tool to a workpiece; and an actuating member moveable in at least first and second degrees of freedom and in operative engagement with both the positioning member and the hydraulic press, and the positioning member being responsive to movement of the actuating member in said first degree of freedom and the hydraulic press being responsive to movement of the actuating member in said second degree of freedom.

17. A linear actuator according to claim 16, wherein the hydraulic pump includes a pump body and a pump piston fitted slidably in a bore in the pump body, and wherein the pump body is attached to the positioning member so that movement of the positioning member relative to the frame member is accompanied by movement of the pump body relative to the frame member.

\* \* \* \* \*